United States Patent
Stüer et al.

(10) Patent No.: US 7,371,890 B2
(45) Date of Patent: May 13, 2008

(54) METHOD FOR THE CONTINUOUS PRODUCTION OF A COMPOUND THAT CARRIES AT LEAST TWO FUNCTIONAL GROUPS

(75) Inventors: Wolfram Stüer, Mannheim (DE); Jens Scheidel, Hirschberg (DE); Hartwig Voβ, Frankenthal (DE); Peter Baβler, Viernheim (DE); Michael Röper, Wachenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 322 days.

(21) Appl. No.: 10/560,740

(22) PCT Filed: Jun. 11, 2004

(86) PCT No.: PCT/EP2004/006297

§ 371 (c)(1),
(2), (4) Date: Dec. 15, 2005

(87) PCT Pub. No.: WO2004/113263

PCT Pub. Date: Dec. 29, 2004

(65) Prior Publication Data

US 2006/0178525 A1    Aug. 10, 2006

(30) Foreign Application Priority Data

Jun. 25, 2003  (DE) ............................... 103 28 715

(51) Int. Cl.
*C07C 67/48* (2006.01)
*C07C 51/42* (2006.01)
*C07C 233/00* (2006.01)
*C07C 255/00* (2006.01)

(52) U.S. Cl. ...................... 560/248; 562/593; 564/216; 558/467

(58) Field of Classification Search ..................... None
See application file for complete search history.

(56) References Cited

U.S. PATENT DOCUMENTS

| 3,013,066 A | 12/1961 | Alderson |
| 4,638,084 A * | 1/1987 | Singleton .................... 560/202 |
| 2005/0288471 A1* | 12/2005 | Bitterlich et al. ........ 526/348.7 |

FOREIGN PATENT DOCUMENTS

| EP | 0 474 386 | 3/1992 |
| FR | 2524341 | 10/1983 |

OTHER PUBLICATIONS

Oehme et al., "An Efficient Palladium(II) Based Catalytic System For The Dimerization of Methyl Acrylate Promoted By Silver Tetrafluoroborate and p-Benzoquinone", Journal of Organometallic Chemistry, No. 320, 1987, pp. C56-C58.
International Search Report No. PCT/EP2004/006297, dated Sep. 22, 2004, 3 pgs.

* cited by examiner

*Primary Examiner*—Karl Puttlitz
(74) *Attorney, Agent, or Firm*—Connolly Bove Lodge and Hutz

(57) ABSTRACT

A process for continuously preparing a compound which bears at least two functional groups which are each independently selected from the group consisting of nitrile group, carboxylic acid group, carboxylic ester group and carboxamide group.

36 Claims, No Drawings

METHOD FOR THE CONTINUOUS PRODUCTION OF A COMPOUND THAT CARRIES AT LEAST TWO FUNCTIONAL GROUPS

The present invention relates to a process for continuously preparing a compound which bears at least two functional groups which are each independently selected from the group consisting of nitrile group, carboxylic acid group, carboxylic ester group and carboxamide group, comprising the steps of
- a) adding two terminal olefin's which bear the functional groups required to prepare the compound as per a1) containing at least two functional groups, in the presence of a compound as per a3) which is suitable as a catalyst for this addition and is homogeneous with respect to the reaction mixture to obtain a mixture comprising
  - a1) a compound which is obtained by monoaddition of the two terminal olefins mentioned and bears at least two functional groups which are each independently selected from the group consisting of nitrile group, carboxylic acid group, carboxylic ester group and carboxamide group,
  - a2) a compound which is obtained by polyaddition of the two terminal olefins mentioned and
  - a3) the compound which is suitable as a catalyst for this addition and is homogeneous with respect to the reaction mixture,
- b) distilling the mixture obtained in step a) to obtain
  - b1) the compound which is obtained by monoaddition of the two terminal olefins mentioned and bears at least two functional groups which are each independently selected from the group consisting of nitrile group, carboxylic acid group, carboxylic ester group and carboxamide group, as the top product and
  - b2) a mixture comprising
    - b2a) a compound which is obtained by monoaddition of the two terminal olefins mentioned and bears at least two functional groups which are each independently selected from the group consisting of nitrile group, carboxylic acid group, carboxylic ester group and carboxamide group,
    - b2b) a compound which is obtained by polyaddition of the two terminal olefins mentioned and
    - b2c) the compound which is suitable as a catalyst for this addition and is homogeneous with respect to the reaction mixture,
- c) separating the entire mixture obtained in step b2) or a portion thereof by means of a semipermeable membrane to obtain a permeate and a retentate, in such a way that the weight ratio of component b2b) to component b2c) in the mixture b2) fed in step c) is smaller than in the retentate,
- d) recycling the permeate obtained in step c) partly or fully into step a) and
- e) recycling the portion of the mixture obtained in step b2) which has not been separated in c) partly or fully into step a).

Numerous compounds which bear two functional groups which are each independently selected from the group consisting of nitrile group, carboxylic acid group, carboxylic ester group and carboxamide group have great industrial significance.

For example, adipic acid or its derivatives constitute important starting compounds for preparing industrially important polymers such as nylon-6 or nylon-6,6.

Such compounds may be obtained, for example, by adding two terminal olefins which bear the functional groups required to prepare the monoolefinically unsaturated compound containing at least two functional groups.

For instance, hexenedioic diester can be prepared by adding acrylic ester in the presence of appropriate catalyst systems, in particular homogeneous rhodium-containing catalyst systems, as described, for example, in J. Organomet. Chem. 1987, 320, C56, U.S. Pat. No. 4,451,665, FR 2,524, 341, U.S. Pat. No. 4,889,949, Organometallics, 1986, 5, 1752, J. Mol. Catal. 1993, 85, 149, U.S. Pat. No. 4,594,447, Angew. Chem. Int. Ed. Engl., 1988, 27. 185, U.S. Pat. No. 3,013,066, U.S. Pat. No. 4,638,084, EP-A-475 386, JACS 1991, 113, 2777-2779, JACS 1994, 116, 8038-8060.

Such an addition of two terminal olefins which bear the functional groups required to prepare the monoolefinically unsaturated compound containing at least two functional groups provides monoolefinically unsaturated compounds which bear at least two functional groups which are each independently selected from the group consisting of nitrile group, carboxylic acid group, carboxylic ester group and carboxamide group. Hydrogenation allows the corresponding saturated compounds to be obtained from such monoolefinically unsaturated compounds.

For a process which can be carried out industrially and is economically viable, it is desirable to be able to continuously carry out the preparation of compounds which bear at least two functional groups which are each independently selected from the group consisting of nitrile group, carboxylic acid group, carboxylic ester group and carboxamide group. The prior art does not disclose such processes.

It is an object of the present invention to provide a process which enables the continuous preparation of a compound which bears at least two functional groups which are each independently selected from the group consisting of nitrile group, carboxylic acid group, carboxylic ester group and carboxamide group, in a technically simple and economically viable manner.

We have found that this object is achieved by the process defined at the outset.

The structures referred to as catalyst in the context of the present invention relate to the compounds which are used as a catalyst; the structures of the catalytically active species under the particular reaction conditions may differ therefrom, but are also included by the term "catalyst" mentioned.

According to the invention, addition in step a) of two terminal olefins which bear the functional groups required to prepare the compound as per a1) containing at least two functional groups, in the presence of a compound as per a3) which is suitable as a catalyst for this addition and is homogeneous with respect to the reaction mixture provides a mixture comprising
- a1) a compound which is obtained by monoaddition of the two terminal olefins mentioned and bears at least two functional groups which are each independently selected from the group consisting of nitrile group, carboxylic acid group, carboxylic ester group and carboxamide group,
- a2) a compound which is obtained by polyaddition of the two terminal olefins mentioned and
- a3) the compound which is suitable as a catalyst for this addition and is homogeneous with respect to the reaction mixture.

In the context of the present invention, a compound a1) refers to a single such compound or to a mixture of such compounds.

In the context of the present invention, a compound a2) refers to a single such compound or to a mixture of such compounds.

In the context of the present invention, a compound a3) refers to a single such compound or to a mixture of such compounds.

The terminal olefins used may advantageously be two identical or different, preferably identical, olefins which each independently have the formula $H_2C=CHR^1$ in which $R^1$ is a nitrile group, carboxylic acid group, carboxylic ester group or carboxamide group, preferably carboxylic ester group or nitrile group.

In the case of the carboxylic ester group, advantageous compounds are esters of aliphatic, aromatic or heteroaromatic alcohols, in particular aliphatic alcohols. The aliphatic alcohols which can be used are preferably $C_1$-$C_{10}$-alkanols, in particular $C_1$-$C_4$-alkanols, such as methanol, ethanol, i-propanol, n-propanol, n-butanol, i-butanol, s-butanol, t-butanol, more preferably methanol.

The carboxamide groups may be N- or N,N-substituted, and the N,N-substitution may be identical or different, preferably identical. Useful substituents are preferably aliphatic, aromatic or heteroaromatic substituents, in particular aliphatic substituents, more preferably $C_1$-$C_4$-alkyl radicals, such as methyl, ethyl, i-propyl, n-propyl, n-butyl, i-butyl, s-butyl, t-butyl, more preferably methyl.

In an advantageous embodiment, the terminal olefin having a functional group which is used may be acrylic acid or its esters. The preparation of acrylic acid, for example by gas phase oxidation of propene or propane in the presence of heterogeneous catalysts, and the preparation of acrylic esters, for example by esterification of acrylic acid with the appropriate alcohols in the presence of homogeneous catalysts such as p-toluenesulfonic acid are known per se.

When acrylic acid is stored or processed, it is customary to add one or more stabilizers which, for example, prevent or reduce the polymerization or the decomposition of acrylic acid, such as p-methoxyphenol or 4-hydroxy-2,2,4,4-tetramethylpiperidine N-oxide ("4-hydroxy-TEMPO").

Such stabilizers can be partly or fully removed before the acrylic acid or its esters are used in the addition step. The stabilizer can be removed by processes known per se, such as distillation, extraction or crystallization.

Such stabilizers may remain in the acrylic acid or its esters in the amount used beforehand.

Such stabilizers may be added to the acrylic acid or its esters before the addition reaction.

When different olefins are used, the addition typically results in mixtures of the different possible addition products.

When one olefin is used, the addition, which in this case is typically referred to as a dimerization, results in one addition product. For economic reasons, this alternative is usually preferred.

In a preferred embodiment, the monoolefinically unsaturated compound which bears at least two functional groups which are each independently selected from the group consisting of nitrile group, carboxylic acid group, carboxylic ester group and carboxamide group is hexenedioic ester, in particular dimethyl hexenedioate, to obtain adipic diester, in particular dimethyl adipate, by hydrogenation.

Adipic acid can be obtained from adipic diester, in particular dimethyl adipate, by cleaving the ester group. Useful processes for this purpose are processes which are for cleaving esters and are known per se.

In a further preferred embodiment, the monoolefinically unsaturated compound which bears at least two functional groups which are each independently selected from the group consisting of nitrile group, carboxylic acid group, carboxylic ester group and carboxamide group is butenedinitrile to obtain adiponitrile by hydrogenation.

In a further preferred embodiment, the monoolefinically unsaturated compound which bears at least two functional groups which are each independently selected from the group consisting of nitrile group, carboxylic acid group, carboxylic ester group and carboxamide group is 5-cyanopentenoic ester, in particular methyl 5-cyanopentenoate, to obtain 5-cyanovaleric ester, in particular methyl 5-cyanovalerate, by hydrogenation.

The addition mentioned of two terminal olefins to obtain the mixture as per step a) may be effected by processes known per se, as described, for example, in J. Organomet. Chem. 1987, 320, C56, U.S. Pat. No. 4,451,665, FR 2,524, 341, U.S. Pat. No. 4,889,949, Organometallics, 1986, 5, 1752, J. Mol. Catal. 1993, 85, 149, U.S. Pat. No. 4,594,447, Angew. Chem. Int. Ed. Engl., 1988, 27. 185, U.S. Pat. No. 3,013,066, U.S. Pat. No. 4,638,084, EP-A475 386, JACS 1991, 113, 2777-2779, JACS 1994, 116, 8038-8060.

The addition reaction may be partial or complete. Accordingly, in the case of partial conversion, the reaction mixture may comprise unconverted olefin.

The addition reaction may advantageously be carried out in the presence of hydrogen. A hydrogen pressure in the range of from 0.1 to 4 MPa has been found to be advantageous.

The addition may advantageously be carried out in the presence of a compound, as a catalyst, which is homogeneous with respect to the reaction mixture and contains rhodium, ruthenium, palladium or nickel, preferably rhodium.

In a preferred embodiment, the mixture obtained in step a) may be hydrogenated between steps a) and b) to obtain a saturated compound.

The hydrogenation may advantageously be carried out in the presence of a substance, as a catalyst, which is heterogeneous with respect to the reaction mixture.

Useful heterogeneous catalysts are preferably those whose catalytically active component is a noble metal of group 8 of the Periodic Table of the Elements, such as palladium, ruthenium, rhodium, iridium, platinum, nickel, cobalt, copper, preferably palladium.

These metals may be used in unsupported form, for example as a suspension catalyst, preferably in the case of nickel or cobalt.

These metals may be used in supported form, for example on activated carbon, metal oxides, transition metal oxides, in particular aluminum oxide, silicon dioxide, preferably as fixed bed catalysts.

The hydrogenation may advantageously be carried out in the presence of a compound, as a catalyst, which is homogeneous with respect to the reaction mixture and contains rhodium, ruthenium, palladium or nickel, preferably rhodium.

In a preferred embodiment, step a) may be carried out in the presence of the same compound, as a catalyst, which is homogeneous with respect to the reaction mixture and contains rhodium as this hydrogenation of the mixture obtained in step a).

In a particularly preferred embodiment, this hydrogenation of the mixture obtained in step a) may be carried out without removing or depleting the homogeneous, rhodium-containing compound used in step a).

This procedure is of great advantage compared to the prior art since no workup of the reaction effluent obtained in the addition reaction mentioned is required. In a particularly preferred embodiment, the mixture obtained in step a) can be transferred without a workup step to this hydrogenation.

This may be effected, for example, by transferring the mixture obtained in step a) from the reaction apparatus into a further apparatus intended for the hydrogenation, i.e. by a spatial separation of step a) and hydrogenation. For example, step a) may be carried out in a reactor such as a stirred tank, a stirred tank battery, or a flow tube, or in a combination of one of these reactor types with a further reactor suitable for the hydrogenation.

This may be effected, for example, by carrying out step a) and hydrogenation successively in the same apparatus, i.e. a temporal separation of step a) and hydrogenation.

Preference is given to carrying out the addition in step a) or the hydrogenation or both in the presence of a compound, as a catalyst, which is homogeneous with respect to the reaction mixture, contains rhodium and has the formula [$L^1RhL^2L^3R$]$^+$X$^-$ where $L^1$ is an anionic pentahapto ligand, preferably pentamethylcyclopentadienyl;

$L^2$ is an uncharged 2-electron donor;

$L^3$ is an uncharged 2-electron donor;

R is selected from the group consisting of H, $C_1$-$C_{10}$-alkyl, $C_6$-$C_{10}$-aryl and $C_7$-$C_{10}$-aralkyl ligands;

X$^-$ is a noncoordinating anion, preferably one from the group consisting of $BF_4^-$, B(perfluorophenyl)$_4^-$, B(3,5-bis(trifluoromethyl)phenyl)$_4^-$, Al(OR$^F$)$_4^-$ where R$^F$ is identical or different part-fluorinated or perfluorinated aliphatic or aromatic radicals, in particular perfluoroisopropyl or perfluoro-tert-butyl;

and where two or three of $L^2$, $L^3$ and R are optionally joined.

In a preferred embodiment, $L^2$ and $L^3$ may each independently be selected from the group consisting of $C_2H_4$, $CH_2$=$CHCO_2Me$, P(OMe)$_3$ and $MeO_2C$—($C_4H_6$)—$CO_2Me$.

In a further preferred embodiment, $L^2$ and $L^3$ may be joined together. In this case, $L^2$ and $L^3$ together may in particular be acrylonitrile or 5-cyanopentenoic ester.

In a further preferred embodiment, $L^2$ and R may be joined together. In this case, $L^2$ and R together may in particular be —$CH_2$—$CH_2CO_2Me$.

In a further preferred embodiment, $L^2$, $L^3$ and R may be joined together. In this case, $L^2$, $L^3$ and R together may in particular be $MeO_2C(CH_2)_2$—(CH—)—($CH_2$)$CO_2Me$.

In a particularly preferred embodiment, the addition in step a) or the hydrogenation or both may be carried out in the presence of a compound, as a catalyst, which is homogeneous with respect to the reaction mixture, contains rhodium and is selected from the group consisting of

[Cp*Rh($C_2H_4$)$_2$H]$^+$BF$_4^-$,
[Cp*Rh(P(OMe)$_3$)($CH_2$=$CHCO_2Me$)(Me)]$^+$BF$_4^-$,
[Cp*Rh(—$CH_2$—$CH_2CO_2Me$)(P(OMe)$_3$)]$^+$BF$_4^-$,
[Cp*Rh($MeO_2C(CH_2)_2$—(CH—)—($CH_2$)$CO_2Me$)]$^+$BF$_4^-$,
[Cp*Rh($C_2H_4$)$_2$H]$^+$B(3,5-bis(trifluoromethyl)phenyl)$_4^-$,
[Cp*Rh(P(OMe)$_3$)($CH_2$=$CHCO_2Me$)(Me)]$^+$B(3,5-bis(trifluoromethyl)phenyl)$_4^-$,
[Cp*Rh(—$CH_2$—$CH_2CO_2Me$)(P(OMe)$_3$)]$^+$B(3,5-bis(trifluoromethyl)phenyl)$_4^-$,
[Cp*Rh($MeO_2C(CH_2)_2$—(CH—)—($CH_2$)$CO_2Me$)]$^+$B(3,5-bis(trifluoromethyl)phenyl)$_4^-$,
[Cp*Rh($C_2H_4$)$_2$H]$^+$B(perfluorophenyl)$_4^-$,
[Cp*Rh(P(OMe)$_3$)($CH_2$=$CHCO_2Me$)(Me)]$^+$B(perfluorophenyl)$_4^-$,
[Cp*Rh(—$CH_2$—$CH_2CO_2Me$)(P(OMe)$_3$)]$^+$B(perfluorophenyl)$_4^-$ and
[Cp*Rh($MeO_2C(CH_2)_2$—(CH—)—($CH_2$)$CO_2Me$)]$^+$B(perfluorophenyl)$_4^-$,
[Cp*Rh($C_2H_4$)$_2$H]$^+$Al(OR$^F$)$_4^-$,
[Cp*Rh(P(OMe)$_3$)($CH_2$=$CHCO_2Me$)(Me)]$^+$Al(OR$^F$)$_4^-$,
[Cp*Rh(—$CH_2$—$CH_2CO_2Me$)(P(OMe)$_3$)]$^+$Al(OR$^F$)$_4^-$ and
[Cp*Rh($MeO_2C(CH_2)_2$—(CH—)—($CH_2$)$CO_2Me$)]$^+$Al(OR$^F$)$_4^-$, where R$^F$ is identical or different part-fluorinated or perfluorinated aliphatic or aromatic radicals, in particular perfluoroisopropyl or perfluoro-tert-butyl.

Such catalysts and their preparation may be effected by processes known per se, as described, for example, in EP-A-475 386, JACS 1991, 113, 2777-2779, JACS 1994, 116, 8038-8060.

The hydrogenation may be carried out in such a way that the monoolefinically unsaturated compound which bears at least two functional groups which are each independently selected from the group consisting of nitrile group, carboxylic acid group, carboxylic ester group and carboxamide group is converted to a saturated compound to obtain the functional groups mentioned. This hydrogenation may advantageously be carried out at a partial hydrogen pressure in the range from 0.01 to 20 MPa. In the hydrogenation, an average mean residence time of the monoolefinically unsaturated compound which bears at least two functional groups which are each independently selected from the group consisting of nitrile group, carboxylic acid group, carboxylic ester group and carboxamide group in the range from 0.1 to 100 hours has been found to be advantageous. In addition, a useful temperature for the hydrogenation is preferably in the range of from 30° C. to 160° C.

The hydrogenation may be carried out in such a way that the monoolefinically unsaturated compound which bears at least two functional groups which are each independently selected from the group consisting of nitrile group, carboxylic acid group, carboxylic ester group and carboxamide group is converted to a saturated compound with hydrogenation of at least one, preferably all, of the functional groups mentioned, more preferably one or more groups selected from carboxylic acid group and carboxylic ester group, in particular carboxylic ester group, in particular with conversion of the group or groups mentioned to one or more groups of the structure —$CH_2OH$. This hydrogenation may advantageously be carried out at a partial hydrogen pressure in the range from 10 to 30 MPa. In the hydrogenation, an average mean residence time of the monoolefinically unsaturated compound which bears at least two functional groups which are each independently selected from the group consisting of nitrile group, carboxylic acid group, carboxylic ester group and carboxamide group in the range from 0.1 to 100 hours has been found to be advantageous. In addition, a useful temperature for the hydrogenation is preferably in the range of from 200° C. to 350° C.

The advantages of the hydrogenation between steps a) and b) become particularly apparent when at least 0.5%, preferably at least 1%, in particular at least 5%, of the monoolefinically unsaturated compound used which bears at least two functional groups which are each independently selected from the group consisting of nitrile group, carboxylic acid group, carboxylic ester group and carboxamide group is hydrogenated to a saturated compound which bears the same at least two functional groups.

According to the invention, the mixture obtained in step a), optionally after a hydrogenation between steps a) and b), is fed to step b) in which the mixture is distilled to obtain b1) the compound which is obtained by monoaddition of the two terminal olefins mentioned and bears at least two functional groups which are each independently selected from the group consisting of nitrile group, carboxylic acid group, carboxylic ester group and carboxamide group, as the top product and b2) a mixture comprising b2a) a compound which is obtained by monoaddition of the two terminal olefins mentioned and bears at least two functional groups which are each independently selected from the group consisting of nitrile group, carboxylic acid group, carboxylic ester group and carboxamide group, b2b) a compound which is obtained by polyaddition of the two terminal olefins mentioned and b2c) the compound which is suitable as a catalyst for this addition and is homogeneous with respect to the reaction mixture.

The distillation in step b) may advantageously be carried out at a bottom temperature in the range from 50 to 200° C., preferably from 60 to 160° C., in particular from 70 to 150° C.

In this case, useful pressures, measured in the bottom of the distillation apparatus, are in the range from 0.05 to 50 kPa, preferably from 0.1 to 10 kPa, in particular from 0.2 to 6 kPa.

Average mean residence times in the range from 1 to 45 minutes, preferably from 5 to 35 minutes, in particular from 10 to 25 minutes, have been found to be advantageous.

Useful apparatus for the distillation is apparatus which is customary for this purpose, as described, for example, in: Kirk-Othmer, Encyclopedia of Chemical Technology, 3rd Ed., Vol. 7, John Wiley & Sons, New York, 1979, page 870-881, such as sieve tray columns, bubble-cap tray columns, columns having structured or random packings, dual-flow tray columns, valve tray columns or one-stage evaporators, such as falling-film evaporators, thin-film evaporators or flash evaporators.

The distillation may be carried out in a plurality of, such as 2 or 3, apparatuses, advantageously a single apparatus.

The component obtained as a top product b1) may, if desired, be worked up or further processed by processes known per se.

When the top product obtained was an unsaturated compound, it may be hydrogenated to a saturated compound by processes known per se. For example, an unsaturated dicarboxylic acid or its ester such as diester, for example butene-dicarboxylic acid or its mono- or diester, may be converted to the corresponding saturated dicarboxylic acid or its ester such as diester, for example adipic acid or its mono- or diester, or to the corresponding, in particular saturated, alcohol, for example hexane-1,6-diol.

When the top product b1) obtained was a diester such as adipic diester or butene-dicarboxylic diester, it may advantageously be reacted, for example, with a terminally unsaturated carboxylic acid such as acrylic acid to obtain a dicarboxylic acid such as butenedicarboxylic acid or adipic acid, and the corresponding ester of the terminally unsaturated carboxylic acid. Such processes are described, for example, in the German application 10240781.9.

According to the invention, the mixture obtained in step b2) is separated in step c) by means of a semipermeable membrane to obtain a permeate and a retentate, in such a way that the weight ratio of component b2b) to component b2c) in the mixture b2) fed in step c) is smaller than in the retentate.

Useful semipermeable membranes are preferably those which have a higher permeability for component b2c) than for component b2b).

Moreover, useful semipermeable membranes are preferably those which have a higher permeability for component b2a) than for component b2b).

A separation layer of the semipermeable membranes may comprise one or more organic or inorganic materials, in particular selected from the group consisting of organic polymer, ceramic materials, metals and carbon or combinations thereof. It should be stable in the feed medium at the filtration temperature.

Useful ceramics are preferably alpha-aluminum oxide, zirconium oxide, titanium dioxide, silicon carbide or mixed ceramic materials.

The organic polymer used may advantageously be polypropylene, polytetrafluoroethylene, polyvinylidene difluoride, polysulfone, polyethersulfone, polyetherketone, polyamide, polyimide, polyacrylonitrile, regenerated cellulose or silicone.

For mechanical reasons, the separation layers are generally applied to a single-layer or multilayer porous substructure made of the same or a different material to the separation layer. The sublayer generally has coarser pores than the separation layer. Examples of advantageous material combinations are listed in the table which follows:

| Separation layer | Sublayer |
| --- | --- |
| Metal | Metal |
| Ceramic | Metal, ceramic or carbon |
| Polymer | Polymer, metal, ceramic or ceramic on metal |
| Carbon | Carbon, metal or ceramic |

The mean average pore size of the membrane should advantageously be in the range from 0.9 to 50 nm, in particular from 3 to 20 nm, in the case of inorganic membranes. The separation limits should preferably be in the range from 500 to 100 000 daltons, in particular in the range from 2 000 to 40 000 daltons, in the case of organic membranes.

The membranes may be used in various geometries, such as flat, tubular, multichannel element, capillary or coil geometry, for which appropriate pressure casings which enable separation between retentate and permeate are available.

The optimum transmembrane pressures are dependent substantially upon the diameter of the membrane pores, the hydrodynamic conditions which influence the cake layer buildup, and the mechanical stability of the membrane at the filtration temperature.

In a preferred embodiment, the transmembrane pressure may be in the range from 0.02 to 10 MPa, in particular from 0.1 to 6 MPa.

The ratio of the pressure on the retentate side to the pressure on the permeate side of the membrane may preferably be in the range from 2 to 100.

On the retentate side, a pressure in the range from 0.1 to 10 MPa may advantageously be applied.

On the permeate side, a pressure in the range from 1 to 1 000 kPa may advantageously be applied.

The membrane separation may be carried out in particular at a temperature in the range from 0 to 150° C.

In order to prevent significant buildup of a cake layer of component b) which leads to a distinct reduction in the permeate flux, it has been found that pumped circulation, mechanical movement of the membrane or stirrer units between the membranes are useful, in particular for generating a relative speed between membrane and suspension in the range from 0.1 to 10 m/s.

The permeate fluxes should advantageously be in the range from 1 to 50 kg/m²/h.

The membrane separation may be effected continuously, for example by single pass through one or more membrane separation stages connected in series.

The membrane separation may be discontinuous, for example by multiple pass through the membrane module.

In the membrane separation, assistants may be used. In this context, the use of component a) or b1) has been found to be advantageous, in particular to the extent to which component a) or b1) has been removed as permeate.

Component a) or b1) may then be removed from the retentate by processes known per se, for example by distillation, extraction, membrane separation, preferably by distillation.

The parameters and apparatus which have already been described for step b) are useful for this purpose.

In a preferred embodiment, the permeate obtained in the process according to the invention may be partly or fully recycled into step a).

In a further preferred embodiment, the mixture b2) obtained in the distillation in accordance with the invention may be fed fully or partly to the membrane separation according to the invention. The substream which is obtained accordingly and is not fed to the membrane separation according to the invention may be partly or fully, preferably fully, recycled into step a).

EXAMPLES

Definitions

Transmembrane pressure:

$$TMP=((P_{module\ inlet}+P_{module\ outlet})/2)-P_{permeate}$$

Solvent exchange coefficient in the diafiltration:

$$MA=\text{diafiltration agent addition (kg)/system capacity (kg)}$$

Example 1

Dimerization of a functionalized olefin, the distillative removal of the homogeneous catalyst and the removal of high boilers by membrane separation A stirred glass autoclave having a capacity of 750 ml and a stirred glass autoclave having a capacity of 400 ml are connected in series as reactors R1 and R2 respectively. With the aid of a pump P1, MA is fed as the reactant to the first autoclave. The feed is via an immersed pipe into the liquid space of R1. Hydrogen is introduced in gaseous form, likewise via this line, using a mass flow regulator F1. The level of R1 is adjusted using a second immersed pipe, which serves as the overflow to R2. Gaseous hydrogen is likewise metered into the overflow line to R2 via a mass flow regulator F2. The feed to R2 is likewise introduced into R2 via an immersed pipe and the effluent from R2 is conducted through a further immersed pipe using a pressure regulating valve from Reco into a thin-film evaporator having an evaporator surface area of 0.046 m². The evaporator is adjusted to a predetermined pressure using a vacuum unit. The evaporator is heated using an oil bath W1. The temperature in W1 is used to control the level in the runoff vessel of the thin-film evaporator. From this vessel, a pump P2 conveys a cycle stream through the evaporator and a further pump P3 conveys a recycle stream from this cycle into the reactor R1, said recycle stream likewise being introduced through the immersed pipe through which the MA feed is also metered in. The pumps P1 and P3 likewise convey the same volumes per unit time. The vapor stream of the evaporator is conducted through an intensive cooler and condensed there. The condensate is subsequently collected (effluent). The constituents which are not condensed under these conditions are subjected to a condensation at atmospheric pressure and collected in a cold trap.

Operation of the continuous dimerization and catalyst removal:

At the start of the experiment, the reactors are charged with the solution which contains $Cp^*Rh(C_2H_4)_2$ and a stoichiometric amount of $HBAr^F_4$ and also 250 ppm of PTZ in HDME. To achieve uniform mixing, the reaction mixture is initially circulated at room temperature for approx. 20 h. Afterward, the thin-film evaporator is preheated to a start temperature of 100° C. The hydrogen stream and the MA feed (120 ml/h, contains 100 ppm by weight of PTZ) are then started, the reactors are heated to 70° C. and the evaporator is operated under reduced pressure.

In the steady state, a rhodium concentration of 190 ppm is determined for R1. In a representative assessment period of 18 h, the following results are obtained:

Feed: 2264 g
Cold trap: 222 g (81% MA)
Effluent: 2036 g (95% unsaturated linear diesters, 4% MA, approx. 0.5% DMA).

After a series of assessments, the proportion of high boilers in the catalyst circuit increases. Therefore, a portion of the recycle stream is discharged and diluted with MA to a total weight of 3002.6 g. The composition of the solution is characterized as follows:

Rh: 16 ppm
High boilers: 65 g/kg (residue determination: evaporation in vacuo at 250° C.)

The solution is subjected to a continuous membrane filtration which is described in detail in example 4.

The MA- and rhodium catalyst-containing permeate for example 4 could be used directly as the feed in the continuous plant for dimerization and thus recycling of the catalyst could be achieved with simultaneous removal of the polymer.

Example 2

Dimerization of a functionalized olefin with the hydrogenation of the C—C double bond of the product with a rhodium catalyst and distillative removal of the homogeneous catalyst and the removal of high boilers by membrane separation A laboratory apparatus as described in example 1 is used, except that the feed is not metered into R1, but rather into R2.

At the start of the experiment, the reactors are charged with a solution which contains $Cp^*Rh(C_2H_4)_2$ and a stoichiometric amount of $HBAr^F_4$ and also 250 ppm of PTZ in HDME. To achieve uniform mixing, the reaction mixture is initially circulated at room temperature for approx. 20 h. Afterward, the thin-film evaporator is preheated to a start temperature of 100° C. The hydrogen stream and the MA feed (120 ml/h, contains 100 ppm by weight of PTZ) are then started, the reactors are heated to 70° C. and the evaporator is operated under reduced pressure. The hydrogen in this example contains 50 ppm of $O_2$.

After several days, a steady state has been attained. In a representative assessment period of 18 h, the following results are obtained.
Rh conc. R1: 175 ppm
Rh conc. R2: 110 ppm Feed: 725 g
Cold trap: 383 g (99% MA)
Effluent: 284 g (63% unsaturated linear diesters, 20% DMA, 17% MA)

The polymer formed may be removed as described in examples 3-5.

Examples 3-5 (Membrane Filtration)

Removal of the homogeneously dissolved rhodium catalyst from high-boiling compounds For the experiments, a thermostattable circulation apparatus having a minimum holdup of 3 l was used.

In the circuit were integrated a reservoir, a pump for pressure generation and flow through the membrane, a heat exchanger to maintain the temperature, a membrane module having incorporated ceramic tubular membrane and a pressure-retaining valve. The permeate runoff was under atmospheric pressure. It was possible using a level control to keep the holdup of the plant constant (diafiltration mode). All reservoirs of the apparatus were inertized with nitrogen. The ceramic tubular membrane used (from Inocermic GmbH) had an external diameter of 10 mm, an internal diameter of 7 mm and a length of 1000 mm. The support element consisted of $Al_2O_3$ and the internally supplied separation layer contained 5 nm pores of $TiO_2$. The flow to the membrane was from the inside and the permeate removed on the outside.

General Experimental Description 3 kg of distillation bottoms were introduced into the circulation vessel, then the pump was started with closed permeate passage and the pressure upstream of the membrane, the transverse flow rate and the temperature were brought to the desired value. The temperature was 40° C. and the transverse flow rate 4 m/s in the membrane tube. The permeate passage was then opened and the supply of the diafiltration medium activated. After a certain permeate removal and the equal supply of diafiltration medium, the experiment was terminated. The retentate use, retentate discharge and the mixed permeate were then analyzed with regard to the high boilers (polymer) and catalyst.

The table which follows contains the results of continuous membrane filtrations, whose parameters have been described above. Example 4 describes the membrane filtration of a substream from example 1.

TABLE 1

Results of the membrane filtrations

| Example No. | TMP (bar) | Permeate flux (kg/m²/h) | Retentate use | | | | Retentate discharge | | | | Diafiltration medium | MA | Permeate discharge | | |
|---|---|---|---|---|---|---|---|---|---|---|---|---|---|---|---|
| | | | m (kg) | Polymer (%) | Rh (ppm) | Rh/Polymer (ppm/%) | m (kg) | Polymer (%) | Rh (ppm) | Rh/Polymer (ppm/%) | | | m (kg) | Polymer (%) | Rh (ppm) |
| 3 | 5 | 13 | 3.2 | 1.0 | 360 | 360 | 3.2 | 1 | 55 | 55 | HDME | 3.4 | 10.8 | n.d. | 92 |
| 4 | 5 | 15 | 3.6 | 6.5 | 16.0 | 2.46 | 3.6 | 6.5 | 3.5 | 0.54 | Methyl acrylate | 2.5 | 9.1 | n.d. | 5.0 |
| 5 | 1 | 18 | 3.0 | 4.8 | 100 | 20.8 | 3.0 | 4.8 | 85 | 17.7 | Acetone | 2.7 | 8.3 | n.d. | 5.5 | n.d. = not detectable

We claim:

1. A process for continuously preparing a compound that contains at least two functional groups which are each independently selected from the group consisting of nitrile group, carboxylic acid group, carboxylic ester group and carboxamide group, the process comprising the steps of
  a) adding two terminal olefins, wherein each of the terminal olefins comprise at least one of the functional groups, to an addition catalyst that is homogeneous with respect to the resulting reaction mixture, the reaction mixture comprising
    a1) the compound is that contains the at least two functional groups and is obtained by monoaddition of the two terminal olefins,
    a2) a compound that is obtained by polyaddition of the two terminal olefins and
    a3) the addition catalyst, the addition catalyst homogeneous with respect to the reaction mixture,
  b) distilling the reaction mixture obtained in step a) to obtain
    b1) the compound by monoaddition of the two terminal olefins as one product and
    b2) a mixture comprising
      b2a) the compound that is obtained by monoaddition of the two terminal olefins,
      b2b) the compound that is obtained by polyaddition of the two terminal olefins and
      b2c) the addition catalyst, the addition catalyst homogeneous with respect to the reaction mixture,
  c) forming a permeate and a retentate by contacting the mixture obtained in step b2) or a portion thereof of to a semipermeable membrane such that a weight ratio of component b2b) to component b2c) in the mixture b2) is smaller than in the retentate,
  d) recycling the permeate obtained in step c) or a portion thereof to step a) and
  e) optionally recycling the portion of the mixture obtained in step b2) that has not been in contact with the membrane in step c) to step a).

2. The process according to claim 1, wherein the compound obtained by monoaddition in the reaction mixture of step a) is hydrogenated between steps a) and b).

3. The process according to claim 1, wherein the addition catalyst comprises rhodium, ruthenium, palladium or nickel.

4. The process according to claim 1, wherein the addition catalyst comprises rhodium.

5. The process according to claim 2, wherein the hydrogenation is conducted in the presence of a hydrogenation catalyst, that is homogeneous with respect to the reaction mixture and comprises rhodium, ruthenium, palladium or nickel.

6. The process according to claim 2, wherein the hydrogenation is conducted in the presence of a hydrogenation catalyst, that is homogeneous with respect to the reaction mixture and comprises rhodium.

7. The process according to claim 2, wherein the addition catalyst and the hydrogenation catalyst are the same compound.

8. The process according to claim 2, wherein the addition catalyst or the hydrogenation catalyst comprises rhodium and has the formula $[L^1RhL^2L^3R]^+X^-$ where
- $L^1$ is an anionic pentahapto ligand;
- $L^2$ is an uncharged 2-electron donor;
- $L^3$ is an uncharged 2-electron donor;
- R is selected from the group consisting of H, $C_1$-$C_{10}$-alkyl, $C_6$-$C_{10}$-aryl and $C_7$-$C_{10}$-aralkyl ligands; and
- $X^{31}$ is a noncoordinating anion; and where two or three of $L^2$, $L^3$ and R are optionally joined.

9. The process according to claim 8, wherein $L^1$ is pentamethylcyclopentadienyl.

10. The process according to claim 8, wherein $X^-$ is selected from the group consisting of $BF_4^-$, B(perfluorophenyl)$_4^-$, B(3,5-bis(trifluoromethyl)phenyl)$_4^-$, Al(OR$^F$)$_4^-$ where $R^F$ is part-fluorinated or perfluorinated aliphatic or aromatic radicals.

11. The process according to claim 8, wherein $L^2$ and $L^3$ are each independently selected from the group consisting of $C_2H_4$, $CH_2$=CHCO$_2$Me, P(OMe)$_3$ and MeO$_2$C—(C$_4$H$_6$)—CO$_2$Me.

12. The process according to claim 8, wherein $L^2$ and $L^3$ together are selected from the group consisting of acrylonitrile and 5-cyanopentenoic ester.

13. The process according to claim 8, wherein $L^2$ and R together are —CH$_2$—CH$_2$CO$_2$Me.

14. The process according to claim 8, wherein $L^2$, $L^3$ and R together are MeO$_2$C(CH$_2$)$_2$—(CH)—(CH$_2$)CO$_2$Me.

15. The process according to claim 8, wherein the addition catalyst or the hydrogenation catalyst comprise rhodium and is selected from the group consisting of
- [Cp*Rh(C$_2$H$_4$)$_2$H]$^+$BF$_4^-$,
- [Cp*Rh(P(OMe)$_3$)(CH$_2$=CHCO$_2$Me)(Me)]$^+$BF$_4^-$,
- [Cp*Rh(—CH$_2$—CH$_2$CO$_2$Me)(P(OMe)$_3$)]$^+$BF$_4^-$,
- [Cp*Rh(MeO$_2$C(CH$_2$)$_2$—(CH—)—(CH$_2$)CO$_2$Me)]$^+$BF$_4^-$,
- [Cp*Rh(C$_2$H$_4$)$_2$H]$^+$B(3,5-bis(trifluoromethyl)phenyl)$_4^-$,
- [Cp*Rh(P(OMe)$_3$)(CH$_2$=CHCO$_2$Me)(Me)]$^+$B(3,5-bis(trifluoromethyl)phenyl)$_4^-$,
- [Cp*Rh(—CH$_2$—CH$_2$CO$_2$Me)(P(OMe)$_3$)]$^+$B(3,5-bis(trifluoromethyl)phenyl)$_4^-$,
- [Cp*Rh(MeO$_2$C(CH$_2$)$_2$—(CH—)—(CH$_2$)CO$_2$Me)]$^+$B(3,5-bis(trifluoromethyl)phenyl)$_4^-$,
- [Cp*Rh(C$_2$H$_4$)$_2$H]$^+$B(perfluorophenyl)$_4^-$,
- [Cp*Rh(P(OMe)$_3$)(CH$_2$=CHCO$_2$Me)(Me)]$^+$B(perfluorophenyl)$_4^-$,
- [Cp*Rh(—CH$_2$—CH$_2$CO$_2$Me)(P(OMe)$_3$)]$^+$B(perfluorophenyl)$_4^-$,
- [Cp*Rh(MeO$_2$C(CH$_2$)$_2$—(CH—)—(CH$_2$)CO$_2$Me)]$^+$B(perfluorophenyl)$_4^-$,
- [Cp*Rh(C$_2$H$_4$)$_2$H]$^+$Al(OR$^F$)$_4^-$,
- [Cp*Rh(P(OMe)$_3$)(CH$_2$=CHCO$_2$Me)(Me)]$^+$Al(OR$^F$)$_4^-$,
- [Cp*Rh(—CH$_2$—CH$_2$CO$_2$Me)(P(OMe)$_3$)]$^+$Al(OR$^F$)$_4^-$ and
- [Cp*Rh(MeO$_2$C(CH$_2$)$_2$—(CH—)—(CH$_2$)CO$_2$Me)]$^+$Al(OR$^F$)$_4^-$,
  where $R^F$ is part-fluorinated or perfluorinated aliphatic or aromatic radicals.

16. The process according to claim 2, wherein the hydrogenation is carried out at a partial hydrogen pressure in the range from 10 to 20,000 kPa.

17. The process according to claim 2, wherein the hydrogenation is conducted at an average mean residence time of the compound that contains the at least two functional groups is from 0.1 to 100 hours.

18. The process according to claim 4, wherein the mixture obtained in step a) is fed to a hydrogenation reaction vessel without removing the addition catalyst.

19. The process according to claim 1, wherein the distillation in step b) is conducted at a temperature in the range from 50 to 200° C.

20. The process according to claim 1, wherein the distillation in step b) is conducted at an average mean residence time in the range from 1 to 45 minutes.

21. The process according to claim 1, wherein the distillation in step b) is conducted at a pressure in the range from 0.5 to 500 mbar.

22. The process according to claim 1, wherein the semipermeable membrane comprises substantially one or more inorganic materials.

23. The process according to claim 22, wherein the mean average pore size of the membrane is from 0.9 to 50 nm.

24. The process according to claim 1, wherein a ratio of the pressure on the retentate side of the membrane to the pressure on the permeate side of the membrane is from 2 to 100.

25. The process according to claim 24, wherein a pressure from 0.1 to 10 MPa is applied on the retentate side of the membrane.

26. The process according to claim 24, wherein a pressure from 1 to 1000 kPa is applied on the permeate side of the membrane.

27. The process according to claim 1, wherein the forming of the permeate and the retentate at the membrane is conducted at a temperature from 0 to 150° C.

28. The process according to claim 1, wherein the compound obtained as b1) in step b) is hydrogenated.

29. The process according to claim 7, wherein the catalyst comprises rhodium.

30. The process according to claim 1, wherein the semipermeable membrane comprises substantially one or more organic materials.

31. The process according to claim 25, wherein a pressure from 1 to 1000 kPa is applied on the permeate side of the membrane.

32. A process for the monoaddition of two terminal olefins, each of said two terminal olefins comprising a functional group independently selected from the group consisting of nitrile, carboxylic acid, carboxylic ester and carboxamide, the process comprising the steps of:
- a) adding the two terminal olefins to an addition catalyst that is homogeneous with respect to the resulting reaction mixture, the reaction mixture comprising;
  - a1) a compound obtained by the monoaddition of the two terminal olefins,
  - a2) a compound obtained by the polyaddition of the two terminal olefins and
  - a3) the addition catalyst;
- b) distilling the reaction mixture obtained in step a) to obtain
  - b1) a top product consisting essentially of the monoaddition product, and
  - b2) a bottom product mixture comprising;
    - b2a) the monoaddition product,
    - b2b) the polyaddition product, and
    - b2c) the addition catalyst, the addition catalyst homogeneous with respect to the bottom product mixture;

c) forming a permeate and a retentate by contacting the bottom product mixture or a portion thereof with a semipermeable membrane to provide a weight ratio of the polyaddition product to the addition catalyst in the retentate that is greater than the same weight ratio in the bottom product mixture; and d) recycling the permeate obtained in step c) or a portion thereof to step a).

33. The process according to claim 32, further comprising e) recycling a portion of the bottom product mixture that does not contact the membrane in step c) to step a).

34. The process according to claim 32, wherein the compound obtained by monoaddition of the two terminal olefins is hydrogenated between step a) and step b) in the presence of a hydrogenation catalyst.

35. The process according to claim 34, wherein the hydrogenation catalyst and the addition catalyst comprise rhodium, and are independently of the formula $[L^1RhL^2L^3R]^+X^-$ where $L^1$ is an anionic pentahapto ligand;

$L^2$ is an uncharged 2-electron donor;

$L^3$ is an uncharged 2-electron donor;

R is selected from the group consisting of H, $C_1$-$C_{10}$-alkyl, $C_6$-$C_{10}$-aryl and $C_7$-$C_{10}$-aralkyl ligands; and $X^-$ is a noncoordinating anion; and where two or three of $L^2$, $L^3$ and R are optionally joined.

36. The process according to claim 31, wherein the membrane has a mean average separation limit of from 500 to 100 000 daltons.

* * * * *